United States Patent
Basu et al.

(10) Patent No.: US 7,379,525 B2
(45) Date of Patent: May 27, 2008

(54) METHOD AND SYSTEM FOR EFFICIENT HELICAL CONE-BEAM RECONSTRUCTION

(75) Inventors: Samit Kumar Basu, Niskayuna, NY (US); Bruno Kristiaan Bernard De Man, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 196 days.

(21) Appl. No.: 11/011,358

(22) Filed: Dec. 15, 2004

(65) Prior Publication Data

US 2006/0126779 A1 Jun. 15, 2006

(51) Int. Cl.
*A61B 6/03* (2006.01)
(52) U.S. Cl. .......................... 378/4; 378/901
(58) Field of Classification Search .............. 378/4–21, 378/901
See application file for complete search history.

(56) References Cited

U.S. PATENT DOCUMENTS

| | | | | |
|---|---|---|---|---|
| 5,504,792 | A * | 4/1996 | Tam | 378/15 |
| 5,825,842 | A * | 10/1998 | Taguchi | 378/15 |
| 6,018,561 | A * | 1/2000 | Tam | 378/4 |
| 6,078,638 | A * | 6/2000 | Sauer et al. | 378/4 |
| 6,084,937 | A * | 7/2000 | Tam et al. | 378/4 |
| 6,118,841 | A * | 9/2000 | Lai | 378/19 |
| 6,233,303 | B1 * | 5/2001 | Tam | 378/4 |
| 6,240,157 | B1 * | 5/2001 | Danielsson | 378/15 |
| 6,292,525 | B1 * | 9/2001 | Tam | 378/4 |
| 6,522,712 | B1 * | 2/2003 | Yavuz et al. | 378/4 |
| 6,574,297 | B2 * | 6/2003 | Tam | 378/15 |
| 6,574,299 | B1 | 6/2003 | Katsevich | 378/15 |
| 6,744,844 | B2 * | 6/2004 | Horiuchi | 378/15 |
| 6,771,733 | B2 * | 8/2004 | Katsevich | 378/4 |
| 6,810,102 | B2 * | 10/2004 | Hsieh et al. | 378/4 |
| 6,819,736 | B1 * | 11/2004 | Bruder et al. | 378/15 |
| 6,856,666 | B2 * | 2/2005 | Lonn et al. | 378/8 |
| 2003/0219093 | A1 * | 11/2003 | Hagiwara | 378/4 |
| 2004/0071257 | A1 * | 4/2004 | Shechter | 378/4 |
| 2006/0039525 | A1 * | 2/2006 | Bontus et al. | 378/4 |

OTHER PUBLICATIONS

Tam et al., Exact (Spiral + Circles) Scan Region-of-Interest Cone Beam Reconstruction via Backprojection, May 2000, IEEE Transaction on Medical Imaging, vol. 19, No. 5.*
Sunnegardh Johan, Iterative Enhancement of Non-Exact Reconstruction in Cone Beam CT, Linkoping University and Siemens AG, MED CTE, Sep. 2004, pp. 54-60.*
Patch, Sarah K., Computation of Unmeasured Third-Generation VCT Views From Measured Views, IEEE Transactions on Medical Imaging, vol. 21. No. 7, Jul. 2002.*

* cited by examiner

*Primary Examiner*—Edward J. Glick
*Assistant Examiner*—Alexander H Taningco
(74) *Attorney, Agent, or Firm*—William E. Powell, III; Curtis B. Brueske

(57) ABSTRACT

A method for reconstructing cone-beam projection data is provided. The method comprises scanning an object in helical mode, wherein the scanning comprises obtaining cone-beam projection data. The method further comprises processing the cone-beam projection data along a plurality of data filtering curves. The processing includes processing the cone-beam projection data along a portion of the data filtering curves that extends outside of a physical detector area to a virtual detector area. Then, the method comprises using the processed cone-beam projection data in the generation of a reconstructed image of the object.

20 Claims, 10 Drawing Sheets

METHOD AND SYSTEM FOR EFFICIENT HELICAL CONE-BEAM RECONSTRUCTION

BACKGROUND

The invention relates generally to the field of image reconstruction in Computed Tomography (CT) imaging systems and more particularly to the field of helical cone-beam reconstruction.

CT systems operate by projecting fan shaped or cone shaped X-ray beams through an object. The X-ray beams are generated by an X-ray source, and are generally collimated prior to passing through the object being scanned. The attenuated beams are then detected by a detector. The detector produces a signal based on the intensity of the attenuated X-ray beams, and the signals are processed to produce projection data. As is known to those skilled in the art, "projection data" refers to a single data point or a collection of data points, wherein each data point represents a line through the object to be imaged. That is, each data point represents the "integral" or "ray sum" along the line, referred to, generally, as a line integral. In CT systems, the line integrals along related lines are grouped, and each group is generally referred to as a projection.

CT systems acquire data continuously, at discrete image view frames corresponding to specific angular positions, as the source and detector rotate about the object being scanned. In helical modes of operation, the data are collected as the object is displaced by movement of the table. The resulting data set contains a large quantity of data points generally indicative of the intensity of radiation received by the detector elements at each of the angular positions. As is known by those skilled in the art, helical cone-beam CT systems have faster scan times and have the potential to cover a patient volume, with just a few gantry rotations, depending on the axial coverage of the detectors.

A computer is generally used to process and reconstruct images of the portions of the object responsible for the radiation attenuation. As will be appreciated by those skilled in the art, these images are computed by processing a series of angularly and translationally displaced projection images. This data is then reconstructed to produce the reconstructed image, which is typically displayed on a cathode ray tube or liquid crystal display, and may be printed or reproduced on film.

A number of exact reconstruction algorithms have been developed for the reconstruction of cone-beam projection data acquired in a helical mode. As is known to those skilled in the art, these algorithms are mathematically exact in the absence of noise and discretization (sampling) effects, and generally produce images of high quality when used on real data. However, known exact reconstruction algorithms are capable of covering only a narrow range of helical pitches or translation speeds of the object. As is known to those skilled in the art, higher pitches or translation speeds are sometimes required in order to meet certain clinical or inspection requirements.

In addition, exact reconstruction algorithms, in general, employ reconstruction windows spanning 360° of angular positions, generally rely upon windows spanning 180° plus the included angle of the X-ray beam (typically referred to as "a"). That is, due to redundancy in the projection data acquired for a window spanning 360° of angular positions, windows spanning 180° plus a generally suffice for image reconstruction. In general, exact reconstruction algorithms, require a scan range of at least 180+the fan angle, α, in order to perform an exact reconstruction of a central image slice. However, as is known to those skilled in the art, while performing a reconstruction of a dynamic internal tissue, such as for example a cardiac segment, in particular, only one or at the most, a few central image slices may be reconstructed (given the fact that only about 180+fan degrees of data is available for performing a cardiac segment reconstruction).

Therefore, there is a need for a technique for extending an exact helical cone-beam reconstruction algorithm to larger helical pitches as well as to adapt an exact helical cone-beam reconstruction algorithm to enable the reconstruction of a large number of images slices with good image quality, using only an angular range corresponding to a cardiac segment acquisition. In addition, there is a need for developing an efficient and accurate technique for performing helical cone-beam backprojection over PI-lines.

SUMMARY

In one exemplary embodiment of the invention, a method for reconstructing cone-beam projection data is provided. The method comprises scanning an object in helical mode, wherein the scanning comprises obtaining cone-beam projection data. The method further comprises processing the cone-beam projection data along a plurality of data filtering curves. The processing includes processing the cone-beam projection data along a portion of the data filtering curves that extends outside of a physical detector area to a virtual detector area. Then, the method comprises using the processed cone-beam projection data in the generation of a reconstructed image of the object.

In another exemplary embodiment, a method for reconstructing cone-beam projection data from an object in cyclic motion is provided. The method comprises scanning the object in helical mode, wherein the scanning comprises obtaining cone-beam projection data. The scanning further comprises a plurality of cycles of which a portion of each cycle captures the object in the same relative position. Then, the method comprises generating a reconstructed image of the object from the cone-beam projection data based upon the portion of each cycle.

In another exemplary embodiment, a method for performing backprojection of processed cone-beam projection data along PI lines is provided. The method comprises performing a scan cycle with a scanner to obtain data needed to reconstruct a plurality of voxels. The method further comprises attaching a state variable to each voxel and comparing the projection of the voxel to a boundary at each projection view. The boundary is a detector area in the scanner comprising an upper detector boundary and a lower detector boundary. Then, the method comprises changing the state variable when the voxel crosses the boundary and computing an updated contribution to the voxel when the state variable changes.

These and other advantages and features will be more readily understood from the following detailed description of exemplary embodiments of the invention that is provided in connection with the accompanying drawings.

DETAILED DESCRIPTION OF EXEMPLARY EMBODIMENTS

Figure 1:
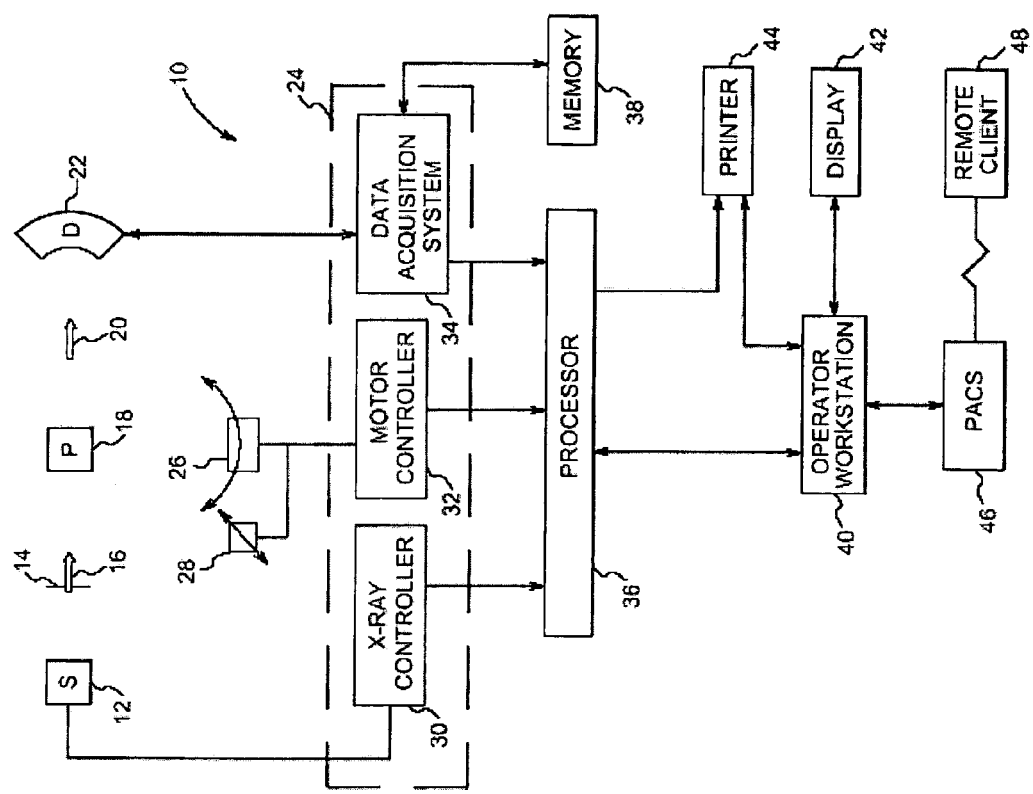
FIG. 1 is a diagrammatical view of an exemplary imaging system in the form of a CT imaging system.

FIG. 1 illustrates diagrammatically an imaging system 10 for acquiring and processing image data. System 10 is a computed tomography (CT) system designed to acquire projection data and reconstruct an image of an object 18 from cone-beam projection data taken on a helical trajectory. Imaging system 10 includes a source of X-ray radiation 12 positioned adjacent to a collimator 14. In this exemplary embodiment, the source of X-ray radiation source 12 is typically an X-ray tube.

Collimator 14 permits a stream of radiation 16 to pass into a region in which an object 18 is positioned. A portion of the radiation 20 passes through or around the object and impacts a detector array, represented generally at reference numeral 22. Detector elements of the array produce electrical signals that represent the intensity of the incident X-ray beam. These signals are acquired and processed to reconstruct an image of the features within the object 18.

Source 12 is controlled by a system controller 24, which furnishes both power, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

System controller 24 is coupled to a linear positioning subsystem 28 and rotational subsystem 26. The rotational subsystem 26 enables the X-ray source 12, collimator 14 and the detector 22 to be rotated one or multiple turns around the object 18. It should be noted that the rotational subsystem 26 may include a gantry. Thus, the system controller 24 may be utilized to operate the gantry. The linear positioning subsystem 28 enables the object 18, or more specifically a table, to be displaced linearly. Thus, the table may be linearly moved within the gantry to generate images of particular areas of the object 18.

Additionally, as will be appreciated by those skilled in the art, the X-ray source 12 may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 26 and the linear positioning subsystem 28.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor 36.

The processor 36 is typically coupled to the system controller 24. The data collected by the data acquisition system 34 may be transmitted to the processor 36 and moreover, to a memory 38. It should be understood that any type of memory to store a large amount of data might be utilized by such an exemplary system 10. Moreover, the memory 38 may be located at this acquisition system or may include remote components for storing data, processing parameters, and routines described below. Also the processor 36 is configured to receive commands and scanning parameters from an operator via an operator workstation 40 typically equipped with a keyboard and other input devices. An operator may control the system 10 via the input devices. Thus, the operator may observe the reconstructed image and other data relevant to the system from processor 36, initiate imaging, and so forth.

A display 42 coupled to the operator workstation 40 may be utilized to observe the reconstructed image and to control imaging. Additionally, the scanned image may also be printed by a printer 44 which may be coupled to the operator workstation 40. The display 42 and printer 44 may also be connected to the processor 36, either directly or via the operator workstation 40. Further, the operator workstation 40 may also be coupled to a picture archiving and communications system (PACS) 46. It should be noted that PACS 46 might be coupled to a remote client 48, radiology department information system (RIS), hospital information system (HIS) or to an internal or external network, so that others at different locations may gain access to the image and to the image data.

It further should be noted that the processor 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
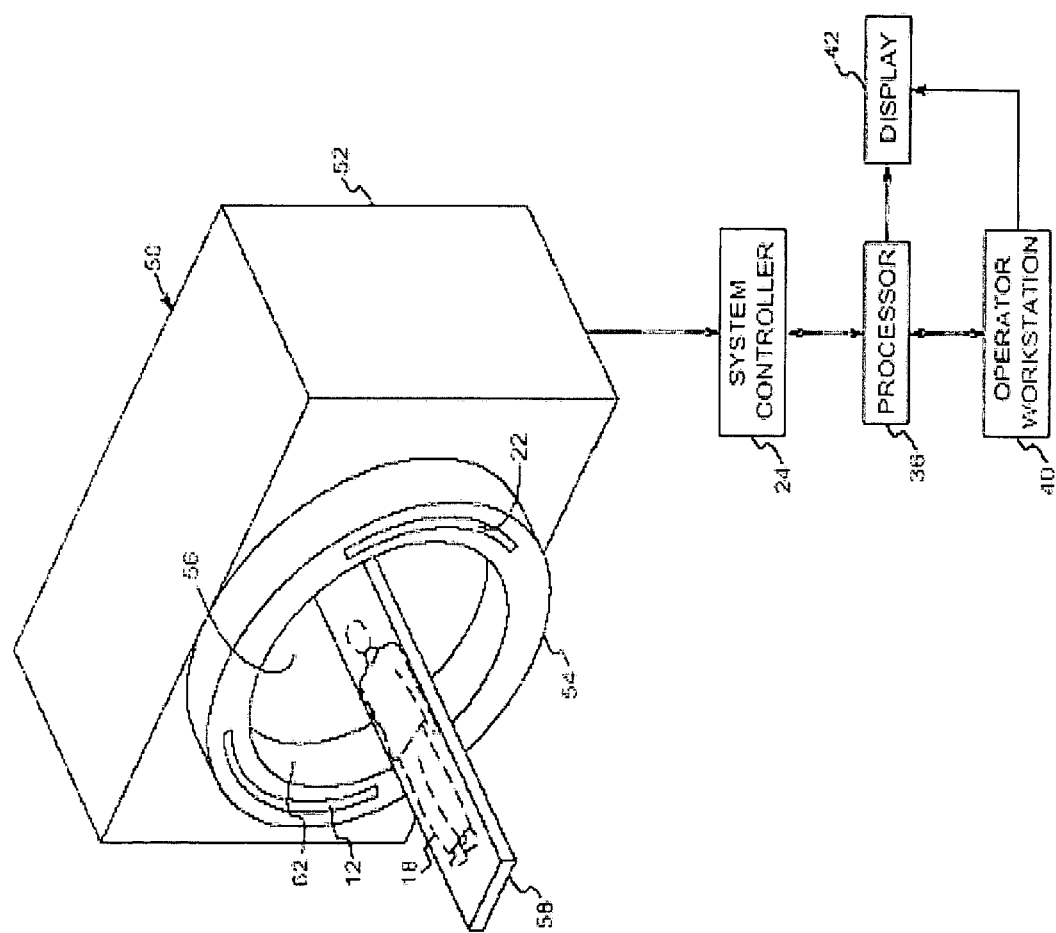
FIG. 2 is another diagrammatical view of a physical implementation of the CT system of FIG. 1.

Referring generally to FIG. 2, an exemplary imaging system utilized in a present embodiment may be a CT scanning system 50. The CT scanning system 50 is typically a multi-slice detector CT (MDCT) or Volumetric CT (VCT) system that offers a wide array of axial coverage, high gantry rotational speed, and high spatial resolution. The CT scanning system 50 is illustrated with a frame 52 and a gantry 54 that has an aperture 56. The aperture 56 may typically be 50 cm in diameter. Further, a table 58 is illustrated positioned in the aperture 56 of the frame 52 and the gantry 54. Additionally, the table 58 is configured to be displaced linearly by the linear positioning subsystem 28 (see FIG. 1). The gantry 54 is illustrated with the source of radiation 12, typically an X-ray tube that emits X-ray radiation from a focal point 62. In typical operation, X-ray source 12 projects an X-ray beam from the focal point 62 toward detector array 22. The detector 22 is generally formed by a plurality of detector elements, which sense the X-rays that pass through and around an object of interest. Each detector element produces an electrical signal that represents the intensity of the X-ray beam at the position of the element at the time the beam strikes the detector. Furthermore, the gantry 54 is rotated around the object of interest so that a plurality of radiographic views may be collected by the processor 36. Thus, an image or slice is computed which may incorporate, in certain modes, less or more than 360 degrees of projection data, to formulate an image. The image is collimated to desired dimensions, using either lead shutters in front of the X-ray source 12 and different detector apertures. The collimator 14 (see FIG. 1) typically defines the size and shape of the X-ray beam that emerges from the X-ray source 12. Thus, as the X-ray source 12 and the detector 22 rotate, the detector 22 collects data of the attenuated X-ray beams. In particular, in accordance with embodiments of the present invention, the X-ray source 12 and the detector 22 cooperate along a helical scanning trajectory of the source 12 to provide cone-beam projection data, as will be described in greater detail with respect to FIG. 3 below.

Data collected from the detector 22 then undergoes pre-processing and calibration to condition the data to represent the line integrals of the attenuation coefficients of the scanned objects. The processed data, commonly called projections, are then filtered and backprojected to formulate an image of the scanned area. As mentioned above, the processor 36 is typically used to control the entire CT system 10. The main processor that controls the operation of the system may be adapted to control features enabled by the system controller 24. Further, the operator workstation 40 is coupled to the processor 36 as well as to a display, so that the reconstructed image may be viewed. Alternatively, some or all of the processing described herein may be performed remotely by additional computing resources based upon raw or partially processed image data. Once reconstructed, the image produced by the system of FIGS. 1 and 2 reveals internal features of the object 18.

Figure 3:
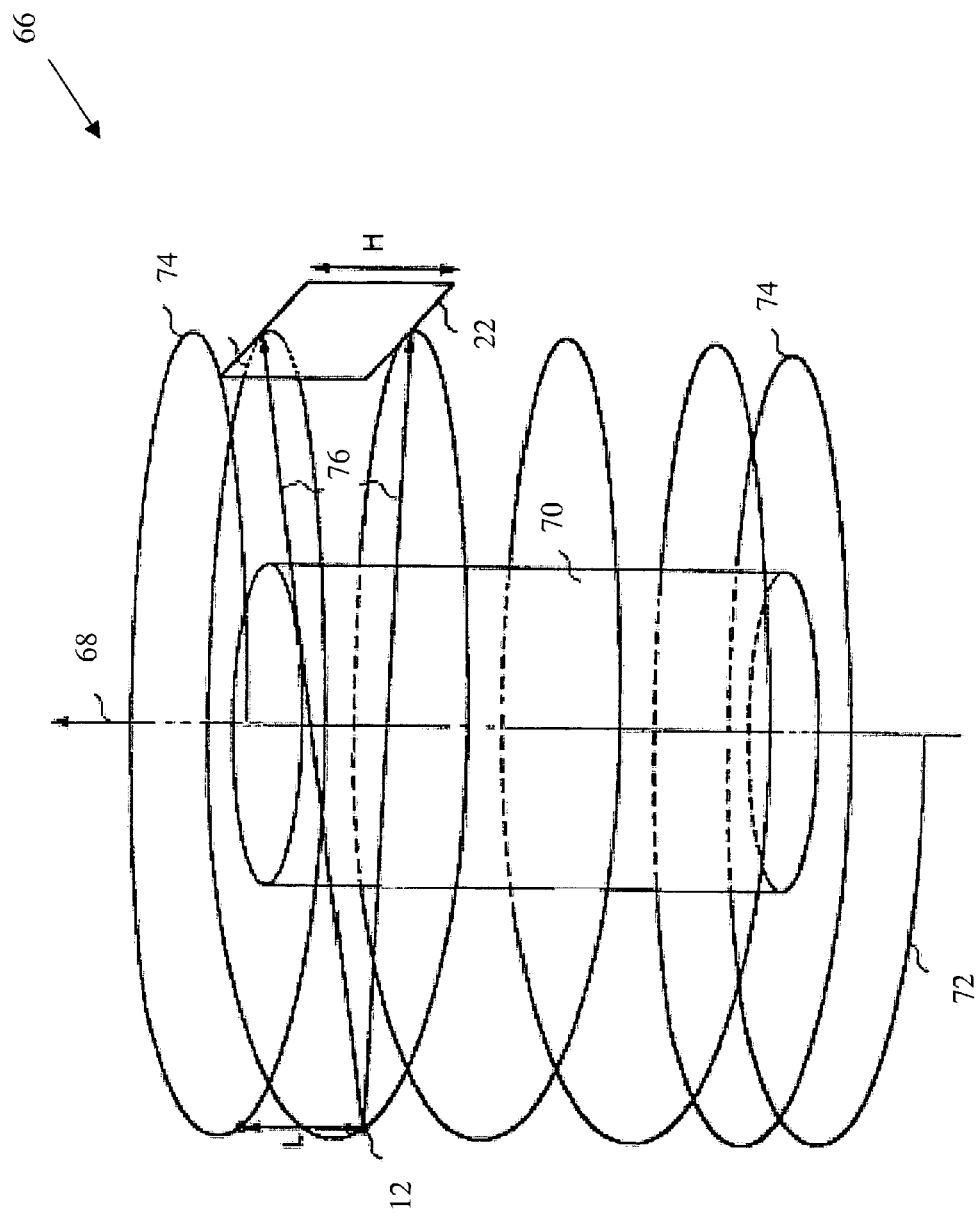
FIG. 3 is an illustration of a typical CT scanner configuration employing helical cone-beam geometry using the CT system of FIG. 1.

FIG. 3 is an illustration of a typical data acquisition configuration employing helical cone-beam geometry using the CT system of FIG. 1. As shown in FIG. 3, a field of view 70 such as a cylinder is radially centered on an axis of rotation 68, and encloses an object to be imaged (not shown in FIG.) or a subsection of an object that extends the size of the field of view 70. The X-ray energy source 12 and the detector 22 cooperate along a helical scanning trajectory 72 of the source 12 to provide cone-beam projection data. The helical scanning trajectory 72 further defines a plurality of turns or revolutions 74 about the axis of rotation 68. Typically, these turns are mutually spaced and surround the field of view 70 such that each plane passing through the field of view 70 intersects the helical scanning trajectory 72 in at least one point. For scanning the object at a plurality of angular positions, the source 12 moves relative to the object and the field of view 70 along the helical scanning trajectory 72, while the detector 22 remains fixed with respect to the source. As a result of the relative movement of the cone-beam source 12 along the helical scanning trajectory 72, the detector 22 acquires corresponding sets of cone-beam projection data to reconstruct the image of the object. As mentioned above, each set of cone-beam projection data is representative of X-ray attenuation caused by the object at different source positions.

The subsequent sections illustrate the various techniques presented by embodiments of the present invention for extending an exact helical cone-beam reconstruction algorithm to larger helical pitches as well adapting an exact helical cone-beam reconstruction algorithm to enable the reconstruction of a large number of images slices with good image quality using only an angular range, wherein the image slices correspond to a cardiac segment acquisition. In addition, embodiments of the present invention disclose an efficient technique for performing helical cone-beam backprojection using PI lines that results in a final image with reduced artifacts.

Figure 4:
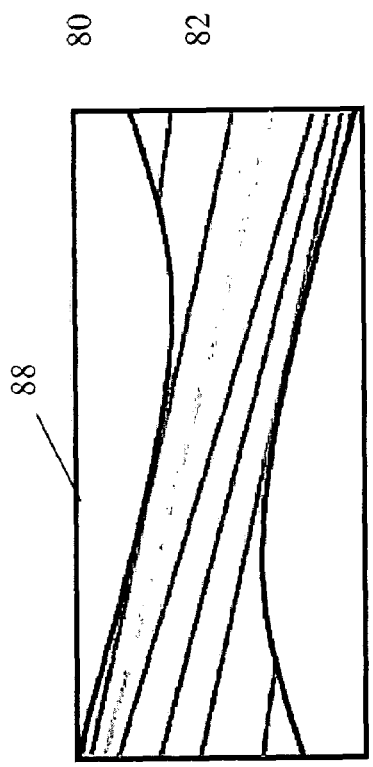
FIG. 4 is an illustration of data filtering curves in a physical detector area comprising the detector of the CT system of FIG. 1.
Figure 5:
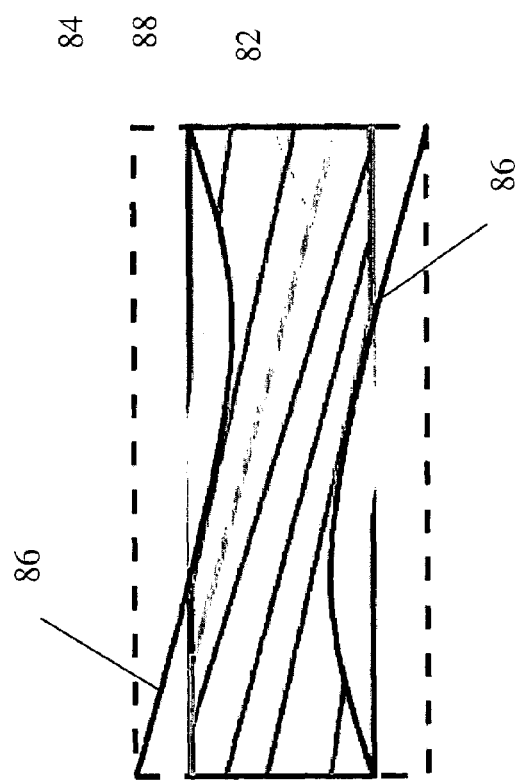
FIG. 5 is an illustration of a portion of data filtering curves that extend outside of the physical detector area, to a virtual detector area.

FIG. 4 and FIG. 5 describe in greater detail, the technique for extending an exact helical cone-beam reconstruction algorithm for reconstructing images of helically scanned objects with larger pitches, in accordance with one embodiment of the invention. As will be appreciated by those skilled in the art, higher helical pitches may be useful in certain cases, for example, to meet certain clinical or inspection requirements. In accordance with this embodiment, the helical mode is a dynamic pitch helical mode.

FIG. 4 is an illustration of data filtering curves in a physical detector area comprising the detector 22 of the CT system of FIG. 1. In accordance with one embodiment, each data filtering curve 82 represents a subset of line integrals (passing through an imaged object) that are used in the reconstruction of the imaged object, as will be described in greater detail below. As will be appreciated by those skilled in the art, a "line integral" measures the integral or "ray sum" along a line and is representative of exactly one projection data point, and vice versa each projection data point represents one particular line through the imaged object. The filtering curves are sparsely represented in FIG. 4. In general, the entire detector is covered with a dense set of filtering curves.

Referring to FIG. 4, the data filtering lines cover a physical detector area 88 comprising the CT scanner 10. However, as the pitch or translation speed increases, the data filtering lines may extend outside of a physical detector area 88 to a virtual detector area as depicted in FIG. 5.

In particular, in accordance with an embodiment, in order to accommodate higher pitches or translation speeds, the cone-beam projection data is processed along the data filtering curves. The processing includes processing the cone-beam projection data along a portion of the data filtering curves that extends outside of the physical detector area 88 to a virtual detector area as will be described in greater detail, with respect to FIG. 5. The processed cone-beam projection data is subsequently used in the generation of a reconstructed image of the object. The reconstruction may be performed using an exact reconstruction algorithm, such as, for example, the Katsevich filtered backprojection algorithm or a non-exact reconstruction algorithm, such as, for example, a modified FDK reconstruction algorithm.

As will be appreciated by those skilled in the art, the Katsevich algorithm for reconstructing an image of an object comprises obtaining measured projection data, identifying a family of data filtering lines on a detector, computing a derivative between neighboring projections, combining this derivative with a weighted derivative taken on the detector, convolving the result with a filter along the family of data filtering lines, and updating the image of the object using the filtered projection data by performing a backprojection operation. The entire process is then repeated for each cone-beam projection until the entire object has been scanned. The helical Feldkamp Davis Kreiss (FDK) technique is an approximate reconstruction algorithm for helical cone-beam geometry and comprises the steps of weighting, filtering and backprojection of data for each projection measurement over the reconstruction volume. The weighting of the projection data is performed with a point-by-point multiplication by a pre-calculated 2D array. The filtering or convolution step filters the image data to decorrelate them and may be carried out as a series of one-dimensional convolutions. In the backprojection step, the projection measurements are added to all voxels in a volume along the lines of the original projection paths.

Referring to FIG. 5, a portion of the data filtering curves, such as, for example, as indicated generally by the reference numeral 86, extends outside of the physical detector area 88 to a virtual detector area 84. In order to accommodate the portion of the filtering curves into the physical detector area 88, embodiments of the present technique process the cone-beam projection data along the portion of the data filtering curves. In one embodiment, the processing comprises manipulating the portion of the data filtering curves 86 so that they fall completely in the physical detector area 88. As used herein, the term "manipulating" refers to extrapolating the detector in the z-direction. In another embodiment, the processing comprises extrapolating the cone-beam projection data along the data filtering curves 82 into the virtual detector area 88.

In accordance with an embodiment, processing the cone-beam projection data may further comprise sampling the projection data along each data filtering curve, wherein each projection data point on the curve is referenced by a unique row coordinate and a unique column coordinate. In one embodiment, the value of the row coordinate of the projection data point is manipulated such that its data value is never larger or smaller than a maximum or minimum value associated with the row coordinates that lie within the physical detector area 88. Then, all the row coordinates whose values are above or below the row coordinates with the maximum or minimum values, are replaced with the maximum or minimum value associated with row coordinates. In an alternate embodiment, the projection data from the last/highest row on the detector, that lies within the physical detector area 88 is synthetically generated and duplicated across the portion of data filtering curves that extend outside of the physical detector area 88.

The processed cone-beam projection data is subsequently used in the generation of a reconstructed image of the object. In particular, the Katsevich filtered backprojection algorithm, as described above, is applied to the processed cone-beam projection data, generated in accordance with aspects of the present technique. That is, the Katsevich algorithm computes a derivative of the processed projection along the data filtering curves 82 and convolutes the computed derivative with a filter along the data filtering curves 82 to generate the reconstructed image of the object.

Therefore, in accordance with an embodiment, a technique is presented wherein an exact helical wide cone-beam reconstruction algorithm may be extended to larger or higher pitches, while maintaining the high quality image reconstruction associated with exact reconstruction algorithms.

In accordance with another embodiment, a method for reconstructing cone-beam projection data of an object in cyclic motion is presented. The method comprises scanning the object in helical mode, wherein the scanning comprises obtaining cone-beam projection data. The reconstructed image of the object is then generated from the cone-beam projection data based upon the portion of each cycle as will be described in greater detail below.

In accordance with this embodiment, the scanning comprises a plurality of cycles of which a portion of each cycle captures the object in the same relative position. In particular, in this embodiment, the object to be imaged is a heart. As will be appreciated by those skilled in the art, since the heart is a moving object, in every cycle, only a small fraction of the acquired projection data belongs to the same "phase" or relative position of the heart and may be used in the reconstruction process, in order to obtain a reasonably good image of the heart. However, since the helical trajectory followed by the X-ray source 12, is typically continuous over the scan range, the resulting projection data that is obtained for image reconstruction is generally representative of a helix comprising missing data segments.

However, as is known to those skilled in the art, in order to perform an exact reconstruction of a given slice, a segment of a helix of a particular length (or that is large enough) to be able to perform reconstruction, is needed. Since only certain segments of the helix are now available for reconstruction, reconstruction of only a limited number of central image slices corresponding to that segment of the helix is possible. That is, each segment of the helix may be typically only large enough to reconstruct a few central slices, which are image slices that are central to the segment. However, it may not be possible to reconstruct slices that are to the left or right of the central slices, since the available portion of the helix to the left or right of the central slices is not sufficiently large and may have missing data.

It would, therefore, be desirable to be able to reconstruct a large number of slices with good image quality, using a limited angular scan range of the object. In accordance with this embodiment, the number of reconstructable slices for a given scan range may be extended or modified, by pre-processing the cone-beam projection data. In one embodiment, the pre-processing initially comprises shifting the cone-beam projection data across a detector row direction. That is, the same segment of the helix is used in the image reconstruction process, but with the projection data shifted by one or a (not necessarily integer) number of detector rows (along the axial direction or z-direction). In order words, the processing of the projection data emulates a longitudinal shift of the imaged object, to generate reconstructed images at different z-positions.

In accordance with an embodiment, shifting the cone-beam projection data comprises generating shifted projection data by applying interpolation and extrapolation to the cone-beam projection data. When the cone-beam projection data is shifted by one detector row, an empty data row (that is a row with missing data) on the detector is generated. In one embodiment, the detector row with missing data is filled up by extrapolating the cone-beam projection data across subsequent detector rows (along a detector row direction). Therefore, the same segment of the helix may be used for reconstructing slices other than the original central slices.

In this manner, the gaps between each reconstructable slice, wherein each reconstructable slice is central to each helix segment, may be considerably reduced, by shifting the projection data by one detector row, along the axial or z-direction, and performing a reconstruction of the object at a new z-position along the detector row. Further, the reconstructed image of the object may be generated using an exact reconstruction algorithm, such as, for example, the Katsevich filtered backprojection algorithm or a non-exact reconstruction algorithm, such as, for example, a modified FDK reconstruction algorithm. In addition, reconstruction weights may be applied to the cone-beam projection data or the shifted projection data or during the backprojection step to further reduce image artifacts.

Figure 6:
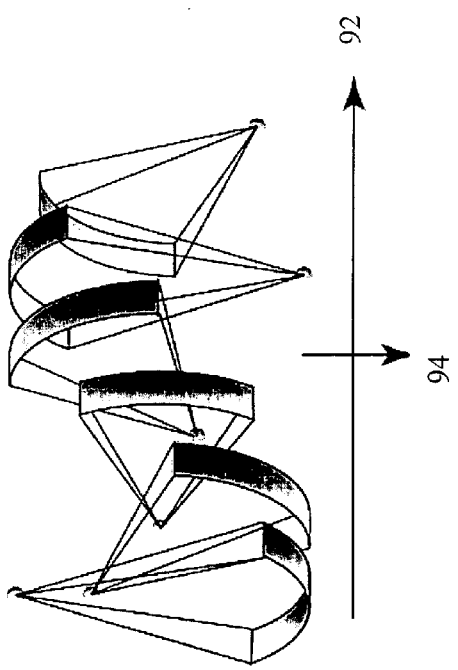
FIG. 6 is an illustration of a range of projections measured at different angular and longitudinal locations relative to an object, imaged using the CT system of FIG. 1, and depicting a central image slice.

FIG. 6 is an illustration of a range of reconstructable image slices of an object, imaged using the CT system of FIG. 1, and depicting a central image slice 94. Reference numeral 92 indicates the axial or z-direction. As may be observed, the central image slice 94 has sufficient amount of helix on either side of the slice in order to perform the reconstruction of only a central slice.

Figure 7:
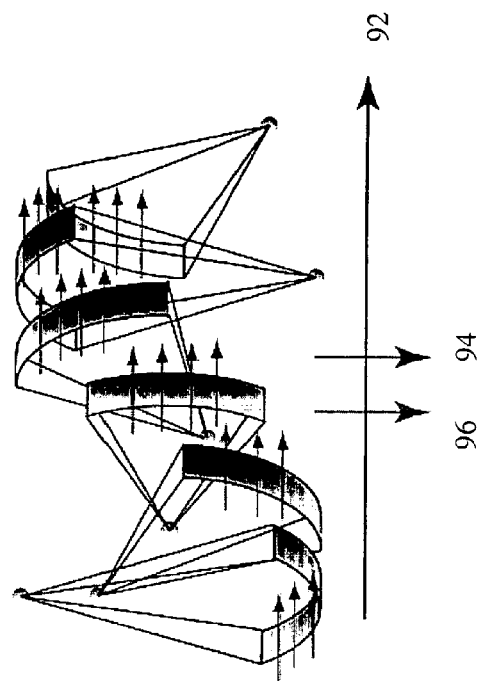
FIG. 7 is an illustration of the technique for generating shifted projection data in accordance with one embodiment.

FIG. 7 is an illustration of the technique for generating shifted projection data in accordance with the present embodiment. As shown in FIG. 7, and as described above, the shifting of the projection data in the z-direction, indicated by the reference numeral 92, results in a reconstruction at a different z-position. Therefore, in accordance with the embodiment described above, a large number of slices with good image quality may be reconstructed, for a given angular scan range of the object, by extending the number of reconstructable slices for a given scan range.

In yet another embodiment of the present invention, an efficient technique for performing backprojection of processed cone-beam projection data along PI lines is disclosed. As is known by those skilled in the art, in the context of a helical acquisition, a PI line is any line that has two points on the source helix trajectory that are less than 360 degrees apart (as seen along the axis of rotation) and a PI segment is the segment of the helix bounded by a PI-line.

Figure 8:
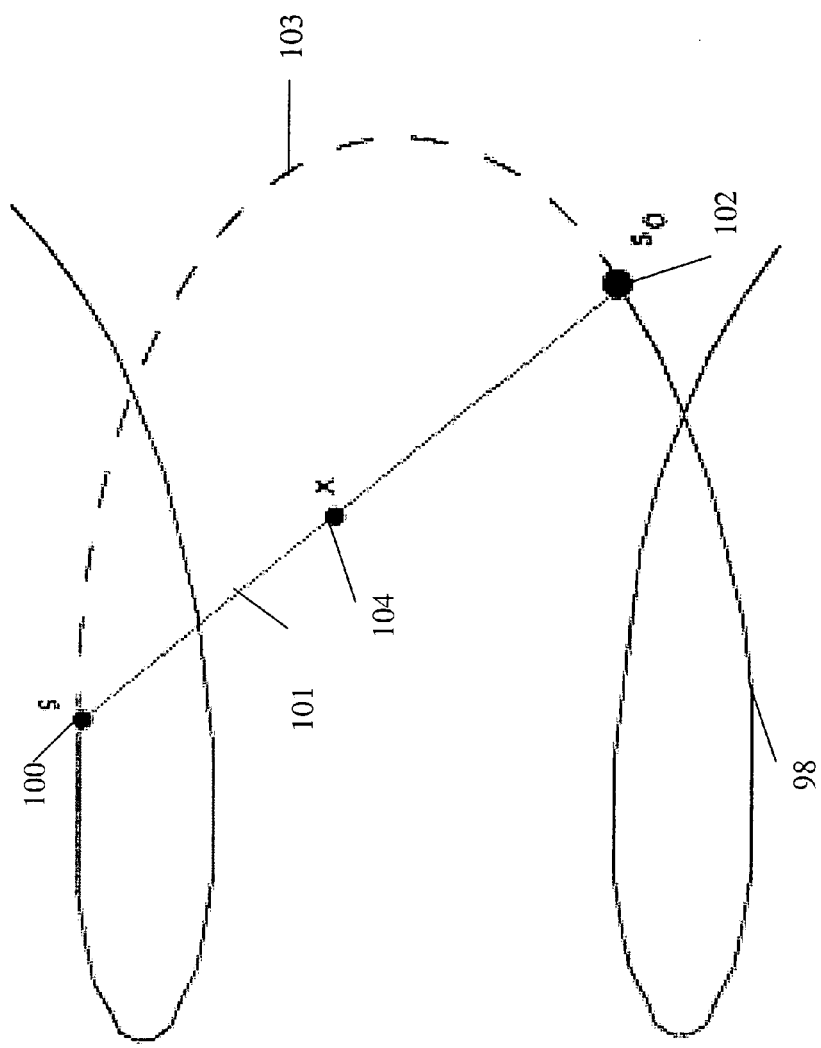
FIG. 8 is an exemplary illustration of a PI line connecting two points on a helix.

FIG. 8 is an exemplary illustration of a PI line connecting two arbitrary points on a helix. As shown in FIG. 8, the PI line is indicated by the reference numeral 101, and connects two points s, 100 and so, 102 on the helix 98. The corresponding PI segment is shown in FIG. 8 with a dashed segment of the helix, and indicated by the reference numeral, 103. The PI segment 103 corresponds to a set of views that contribute to the reconstruction of the voxel, x, denoted by the reference numeral 104. As will be appreciated by those skilled in the art, for performing a PI line backprojection, a single value, in principle, is replicated across all voxels on the PI line 101.

As is known to those skilled in the art, a number of algorithms that have been developed for reconstruction from cone beam projection data taken on a helical trajectory require one or more of: a PI-interval backprojection, which is a backprojection over the entire PI-interval, and a PI-line backprojection, which is backprojection only along PI-lines. As used herein, the "PI-interval" is defined by the segment of the helix, whose end-points define a line that passes through the voxel under consideration, and the PI line, as described above, refers to any line that has two points on the helix less than 360 degrees apart.

A number of solutions have been proposed for performing backprojection of processed cone-beam projection data over a PI-interval. One solution is to convert the PI-interval integral into a Tam-windowed regular backprojection. In this method, the detector image (after filtering) is multiplied by a mask so that detector samples outside the Tam boundary are set to zero. The result is that during the backprojection process, voxels that are projected outside the Tam boundary (or equivalently, the corresponding view is outside the PI interval of this voxel) receive a zero contribution. This approach generally leads to poor images because of mask boundaries. In some cases, smoothing of the detector boundary may be performed, but this technique still yields artifacts in the final reconstructed image. A second approach is to pre-calculate the PI interval for each voxel in the reconstruction, and then for each voxel, to loop over all views in the PI interval to perform the backprojection. However, this approach leads to an inefficient backprojection, as large sections of projection data must be indexed at one time.

Similar approaches exist for the case of backprojecting along PI lines only. One approach is to window the detector with a mask that zeros out both the inside and outside of the detector, leaving only the boundary. The windowing or masking of the detector involves a point by point multiplication of the detector image by the mask image. The mask introduces artifacts into the backprojection, even when smoothed. Another approach is to loop over PI lines, and use a ray-driven backprojector for these terms. In a ray-driven backprojector, a line is traced from one terminus of the PI-segment to the other terminus. One then steps along the line, entering a new voxel (or set of voxels) with each step. These voxels are updated with the value for the PI-line. However, it is generally not feasible to match the resolution of this backprojection with the voxel-driven backprojection used for the PI-segment backprojections, resulting in artifacts in the imaged object.

In accordance with an embodiment, the technique for performing backprojection of processed cone-beam projection data along PI lines comprises performing the backprojection of each voxel, one or more projection views at a time, using a voxel-driven approach. In particular, a PI-interval backprojection as well as a PI-line backprojection is performed one projection view at a time. "PI-interval backprojection" refers to performing a backprojection of a voxel, wherein a voxel value is updated if the projection of the voxel falls inside the detector boundaries and "PI-line backprojection" refers to performing a backprojection of a voxel, wherein a voxel value is updated if the projection of the voxel falls on the detector boundaries.

Figure 9:
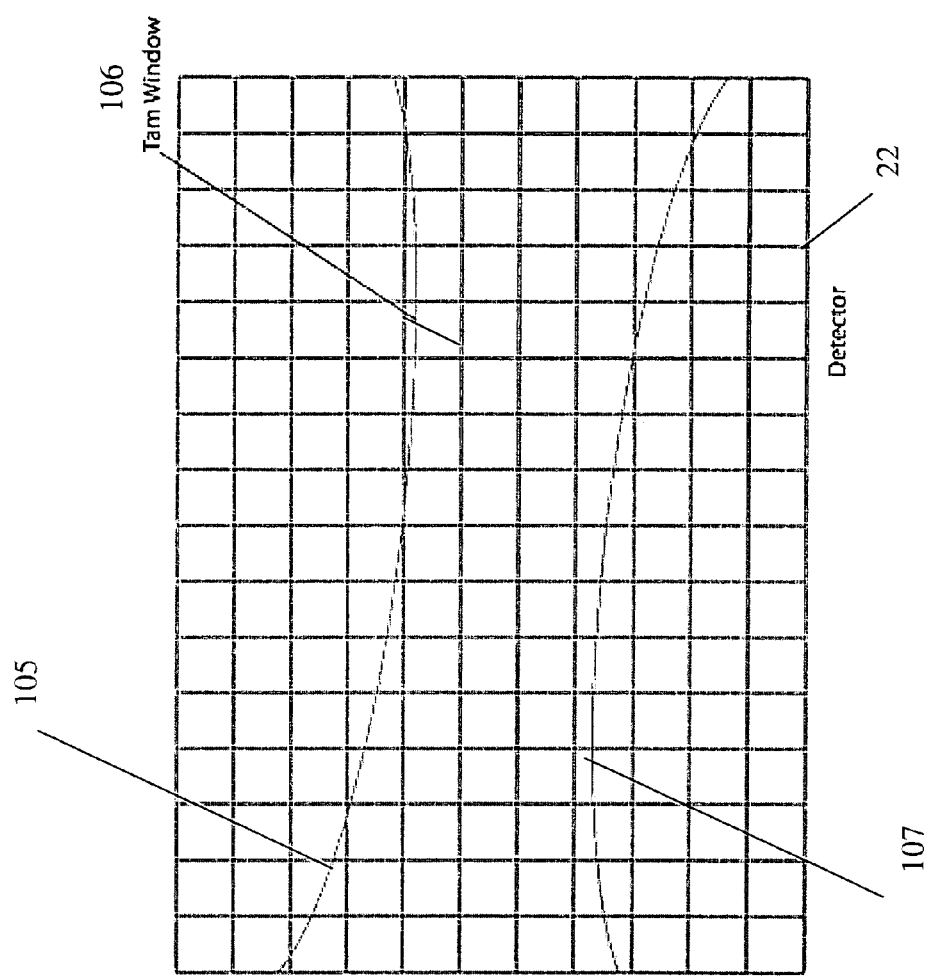
FIG. 9 is an exemplary illustration of a Tam window.

FIG. 9 is an exemplary representation of a Tam window. As shown in FIG. 9, the Tam window or boundary is indicated by the reference numeral 106. The Tam boundary comprises an upper detector boundary 105 and a lower detector boundary 107. The Tam boundary is defined as the projection of the source helix onto the detector, wherein the projection is defined through the current source point.

Figure 10:
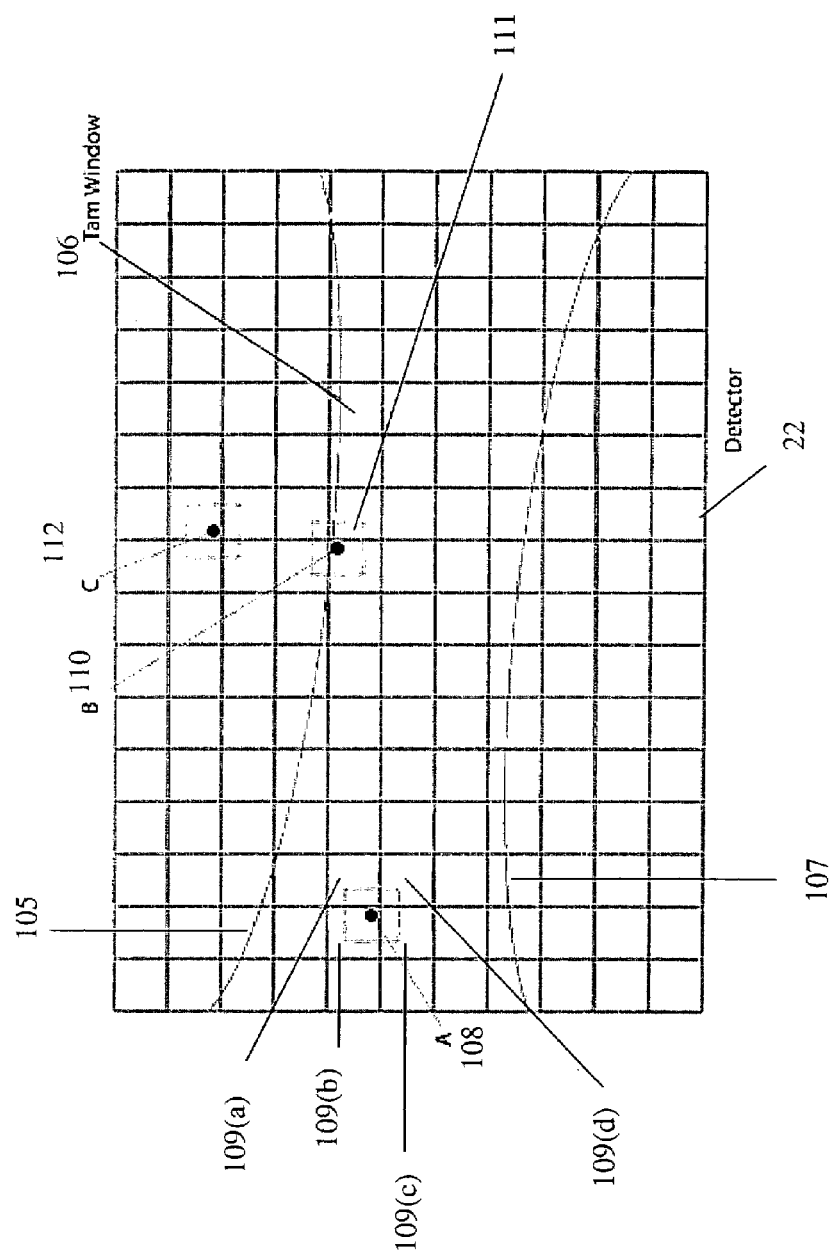
FIG. 10 is an illustration of three reconstruction points projected onto the detector of the CT system of FIG. 1.

FIG. 10 is an illustration of three reconstruction points projected onto the detector of the CT system of FIG. 1. For performing a PI-interval backprojection in accordance with the present embodiment, for each view and each voxel, the projection of the voxel is tested against the Tam window 106, or against an approximation of the boundary. As used herein, an "approximation of the boundary" refers to, for example, a polynomial function of suitable order and with adequately chosen coefficients so as to approximate the true boundary, but with a lower computational cost per hit test. Further, in accordance with the present embodiment, if the projection of the voxel falls within the boundary 106, a specific value (which is an updated value) of the voxel is computed via interpolation from the unmasked detector image. If the projection falls outside the boundary, the voxel value is not updated. When the loop over all projection views is complete, each voxel effectively integrates over its respective PI interval. As shown in FIG. 10, point A, indicated by the reference numeral 108, falls inside the Tam window 106, as do four discrete detectors (referenced, generally, by the reference numerals, 109(a), 109(b), 109(c) and 109(d) used to interpolate a value for A. Point B indicated by the reference numeral, 110, falls close to the border but is still inside the Tam boundary 106, although some of the points used in its interpolation (indicated in FIG. 10 by a box 111) are outside the boundary. Point C, indicated by the reference numeral, 112 falls outside the Tam boundary 106, and is excluded by aspects of this technique.

Figure 11:
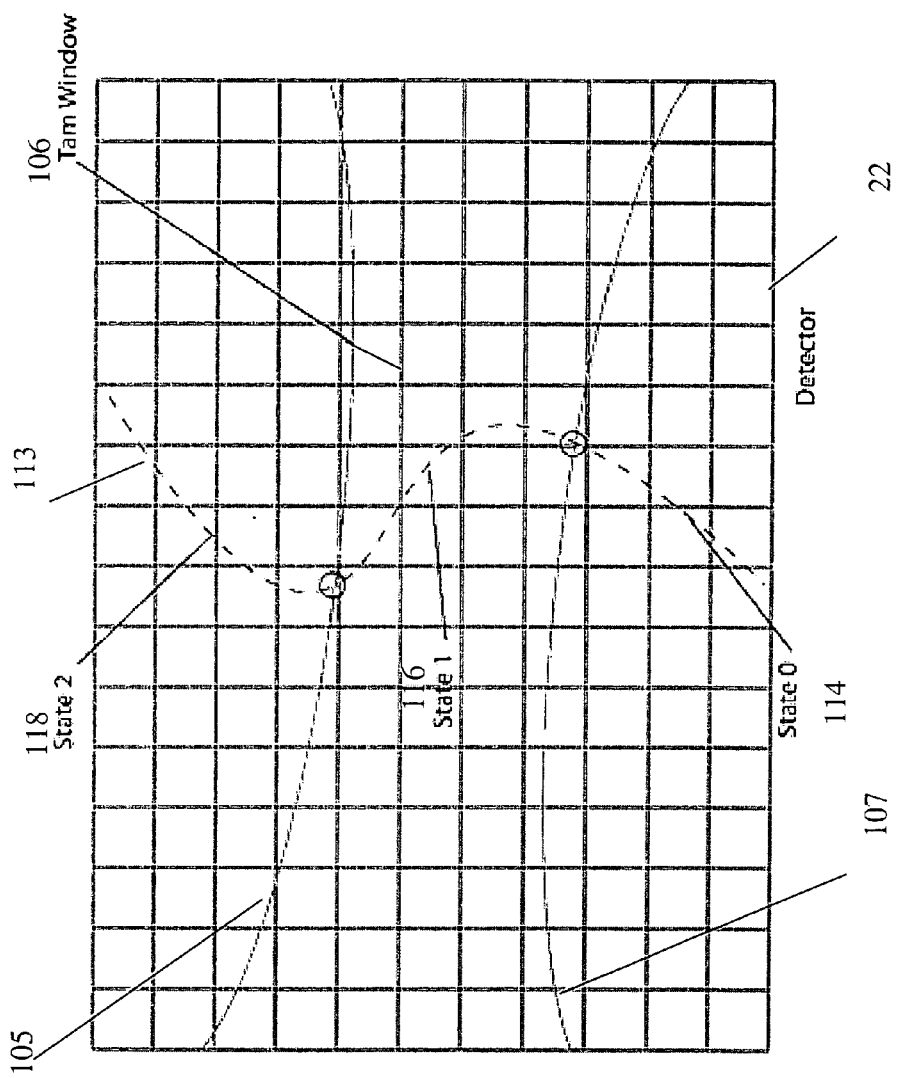
FIG. 11 is an illustration of the trajectory of a sample voxel onto the detector of the CT system of FIG. 1, showing three state regions.

FIG. 11 is an illustration of the trajectory of a sample voxel onto the detector of the CT system of FIG. 1, showing three state regions and indicating the technique for performing a PI-line backprojection in accordance with aspects of the present technique. For performing a PI-line backprojection, each voxel is associated with a state. The state determines if the voxel is below the lower Tam boundary 107, in the Tam window 106, or above the upper Tam boundary 105. Therefore, in accordance with aspects of the present embodiment, each voxel is identified by its actual value as well as a state that indicates the position of the voxel, with respect to the detector boundaries.

Assuming that the helical scanning trajectory is such that the voxel moves from the bottom of the detector to the top of the detector, all voxels are initialized with a first state (denoted by a state 0). With each projection view, each voxel is compared against the Tam boundary 106 and the state is adjusted accordingly. When the state changes, a contribution is added to the voxel. Hence, each voxel is updated exactly twice, once when the voxel crosses the lower boundary 107 and once when the voxel crosses the upper boundary 105. Further, to determine the exact location at which a voxel crosses the upper and lower detector boundaries, the value of the row and column detector coordinates at which each voxel crosses the lower and upper detector boundaries is initially determined. Therefore, there exists exactly two projection views or CT views for each of the detector boundaries, a first CT view when the voxel is below the lower detector boundary 107, and a second CT view when the voxel crosses the lower detector boundary 107. Similarly, there exist exactly two projection views or CT views for the upper detector boundary 105, a first CT view when the voxel is below the upper detector boundary 105, and a second CT view when the voxel crosses the upper detector boundary 105. The exact location at which each voxel crosses the detector boundaries is then determined either by determining the coordinates at which the voxel is projected in the second CT view, or by interpolating between the coordinates of the voxel that correspond to the projection of the voxel in the first and second CT views. As will be appreciated by those skilled in the art, for the creation of an artifact free image, an essential requirement for algorithms that perform backprojection along PI lines is that each voxel is updated exactly twice. Furthermore, in accordance with the present embodiment, the techniques of performing PI-Interval backprojection and PI-line backprojection may be combined in an efficient implementation, wherein only one comparison between the projected voxel location and the Tam boundary is performed for each projection view.

Referring to FIG. 11 again, a PI-line backprojection is shown, indicating three state regions. The dotted curve, indicated by the reference numeral 113 is an exemplary trajectory of a sample voxel on the detector with the progression of a helical scan. The state associated with the voxel is indicated in each of the three regions, as well as the two points at which contributions to the voxel are made. State 0, indicated by the reference numeral 114, indicates that the projection of the voxel is below the lower Tam boundary 107. State 1, indicated by the reference numeral 116, indicates that the projection of the voxel is between the boundaries, and state 2, indicated by the reference numeral 118, indicates that the projection of the voxel is above the upper boundary 105. The state of a voxel changes exactly twice, forcing each voxel to belong to a unique PI-line.

Figure 12:
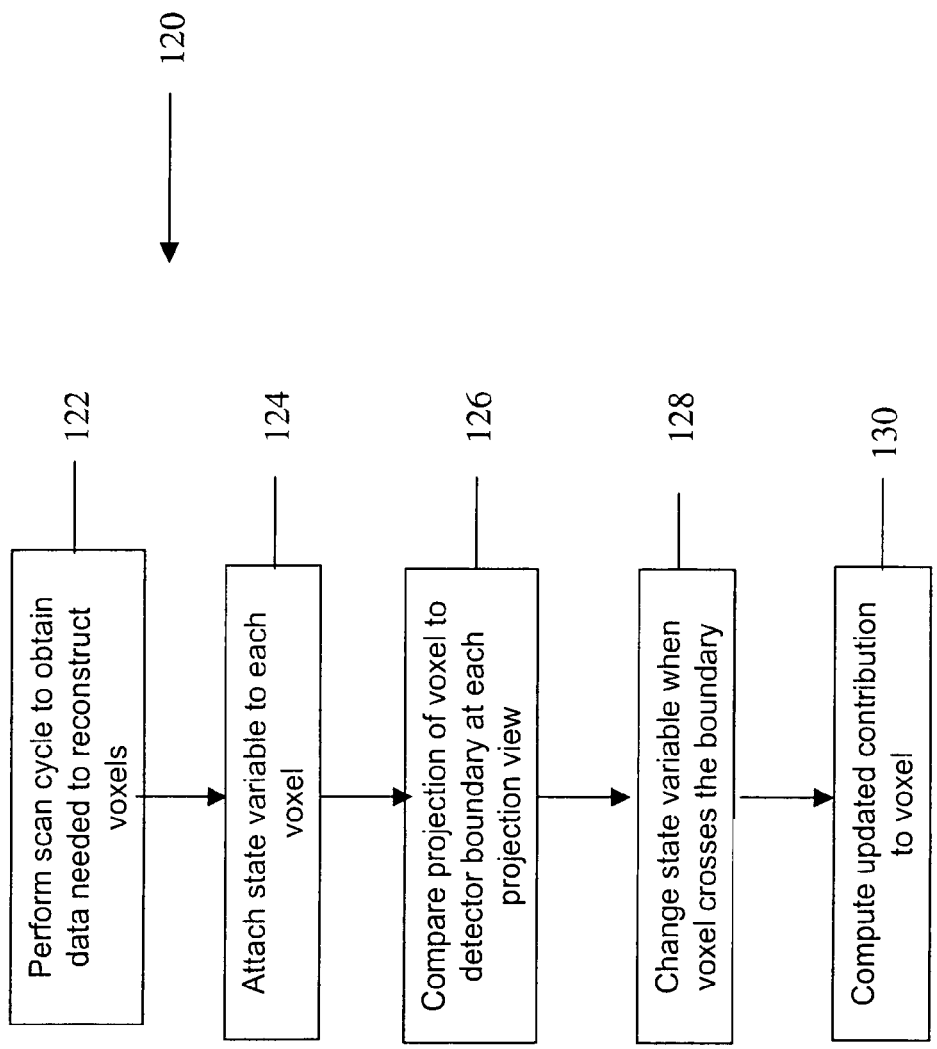
FIG. 12 is a high level flowchart, describing exemplary steps for performing backprojection along PI lines in accordance with aspects of the present technique.

FIG. 12 is a high level flowchart, describing exemplary steps for performing backprojection along PI lines. At step 122, a scan cycle with a scanner, such as from the CT system depicted in FIG. 1, is performed to obtain data needed to reconstruct a plurality of voxels. At step 124, a state variable to each voxel is attached. At step 126, the projection of the voxel is compared to the detector boundaries at each projection view. At step 128, the state variable attached to the voxel is changed when the voxel crosses either the upper or lower detector boundaries in a manner as described above. At step 130, an updated contribution to the voxel is computed when the state variable changes.

The above embodiment therefore provides an efficient technique for performing backprojection using PI lines. In addition, both PI-Interval and PI-Line backprojection may be performed one view at the same time, which is ideal for hardware and efficient software implementations. The voxel update values are interpolated from unmasked detector images, resulting in accurate (artifact free) backprojections. For PI-interval backprojection, a voxel-driven backprojection for cone-beam helical is combined with a per-voxel per-view test against the Tam boundary. Voxel update values are then obtained via interpolation from an unmasked detector image. For the PI-line backprojection, every voxel receives exactly two contributions (forced by the state changes), which ensures that every voxel is assigned to only one PI-line after discretization. In addition, for performing the PI-line backprojection, a voxel driven cone-beam back projector is combined with a state variable for each voxel. The state tracks whether the pixel is below the lower Tam boundary, between the Tam boundaries, or above the upper Tam boundary. With each view, the state is updated based on the location of the projected voxel onto the detector. Updates are made to the voxel value only when the state changes.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

The invention claimed is:

1. A method for reconstructing cone-beam projection data, comprising:
    scanning an object in helical mode, wherein the scanning comprises obtaining cone-beam projection data;
    processing the cone-beam projection data along a plurality of data filtering curves, wherein the processing includes processing the cone-beam projection data along a portion of the data filtering curves that extends outside of a physical detector area to a virtual detector area; and using the processed cone-beam projection data in the generation of a reconstructed image of the object.

2. The method of claim 1, wherein the helical mode is a dynamic pitch helical mode.

3. The method of claim 1, wherein the cone-beam projection data is acquired by an X-ray Computed Tomography (CT) scanner.

4. The method of claim 1, wherein the processing comprises manipulating the portion of the data filtering curves so that they fall completely in the physical detector area.

5. The method of claim 1, wherein the processing comprises extrapolating the cone-beam projection data along the plurality of data filtering curves into the virtual detector area.

6. The method of claim 1, wherein the reconstructed image of the object is generated using a Katsevich filtered backprojection algorithm.

7. The method of claim 1, wherein the reconstructed image of the object is generated using a modified FDK reconstruction algorithm.

8. A method for reconstructing cone-beam projection data of an object, the method comprising:
   scanning the object in helical mode, wherein the scanning comprises obtaining cone-beam projection data, and wherein less than one hundred percent of the cone-beam projection data is available for image reconstruction, resulting in a limited range of reconstructable image slices;
   pre-processing the cone-beam projection data to form pre-processed cone-beam projection data, wherein said pre-processing the cone-beam projection data comprises shifting the cone-beam projection data across a detector row direction; and
   generating a reconstructed image of the object from the pre-processed cone-beam projection data.

9. The method of claim 8, wherein the cone-beam projection data is acquired by an X-ray Computed Tomography (CT) scanner.

10. The method of claim 8, wherein the object is a heart and wherein the scanning comprises a plurality of cycles of which a portion of each cycle captures the object in the same relative position corresponding to the limited range of reconstructable image slices.

11. The method of claim 8, wherein shifting the cone-beam projection data comprises generating shifted projection data by applying interpolation and extrapolation to the cone-beam projection data.

12. The method of claim 11, further comprising applying weights to the cone-beam projection data.

13. The method of claim 11, further comprising applying weights to the shifted projection data.

14. The method of claim 8, wherein pre-processing the cone-beam projection data comprises extrapolating the cone-beam projection data across a detector row direction.

15. The method of claim 8, wherein the reconstructed image of the object is generated using a Katsevich filtered backprojection algorithm.

16. A method for performing backprojection of processed cone-beam projection data along PI lines comprising:
   performing a scan cycle with a scanner to obtain data needed to reconstruct a plurality of voxels;
   attaching a state variable to each voxel;
   comparing the projection of the voxel to a boundary at each projection view, wherein the boundary is a detector area in the scanner comprising an upper detector boundary and a lower detector boundary;
   changing the state variable when the voxel crosses the boundary; and
   computing an updated contribution to the voxel when the state variable changes.

17. The method of claim 16, wherein the boundary is the projection of a helix.

18. The method of claim 16, wherein the boundary is a Tam detector boundary.

19. The method of claim 16, wherein the state variable tracks a trajectory of the projection of the voxel at the boundary of the detector area.

20. A method for performing backprojection of processed cone-beam projection data over a PI interval, comprising:
   performing a scan cycle with a scanner to obtain data needed to reconstruct a plurality of voxels;
   attaching a state variable to each voxel;
   comparing the projection of the voxel to a boundary at each projection view, wherein the boundary is a detector area in the scanner comprising an upper detector boundary and a lower detector boundary;
   changing the state variable when the voxel crosses the boundary; and
   computing an updated contribution to the voxel when the state variable has a specific value.

* * * * *